United States Patent

Syrjänen

[19]

[11] Patent Number: 5,828,720
[45] Date of Patent: Oct. 27, 1998

[54] EXPOSURE AUTOMATICS FOR AN X-RAY APPARATUS

[75] Inventor: Timo Juhani Syrjänen, Espoo, Finland

[73] Assignee: Orion-Yhtyma OY, Espoo, Finland

[21] Appl. No.: 762,754

[22] Filed: Dec. 10, 1996

[30] Foreign Application Priority Data

Dec. 14, 1995 [FI] Finland ................................. 956003

[51] Int. Cl.⁶ ....................................................... A61B 6/14
[52] U.S. Cl. ............................................. 378/38; 378/108
[58] Field of Search .................... 378/108, 38, 39–40, 378/168

[56] References Cited

U.S. PATENT DOCUMENTS

| | | |
|---|---|---|
| 4,021,672 | 5/1977 | Franke . |
| 4,035,650 | 7/1977 | Franke ..................... 378/168 |
| 4,475,224 | 10/1984 | Grassme . |
| 4,486,896 | 12/1984 | Richter et al. ........................... 378/108 |
| 4,589,121 | 5/1986 | Makino . |
| 4,748,648 | 5/1988 | Boucle et al. ........................... 378/108 |
| 4,813,060 | 3/1989 | Heubeck et al. . |
| 4,815,115 | 3/1989 | Nieminen et al. . |
| 5,386,448 | 1/1995 | Tammisalo et al. . |
| 5,425,065 | 6/1995 | Järvenin . |

FOREIGN PATENT DOCUMENTS

| | | |
|---|---|---|
| 0 229 972 | 7/1987 | European Pat. Off. . |
| 69559 | 11/1985 | Finland . |
| 76234 | 5/1988 | Finland . |
| 90183 | 9/1993 | Finland . |
| 90617 | 11/1993 | Finland . |

*Primary Examiner*—Craig E. Church
*Attorney, Agent, or Firm*—Pennie & Edmonds LLP

[57] ABSTRACT

Equipment for automatic adjustment of image receptor exposure during imaging in panoramic or tomographic radiography. The equipment includes: a radiation source (4) and an image receptor (7), the radiation (5) passing through the object (6) to be X-ray examined, placed between these; at least two interspaced detectors (1), placed behind the image receptor and measuring the radiation intensity; memory means for storing exposure reference values; and adjustment means (3), which adjust variables affecting the image receptor exposure during X-raying on the basis of signals from the detectors and reference values. The apparatus also includes an integrator for each separate detector (1a, 1b, 1c, . . . ) or detector array, connected directly to the detector outputs, whereby a measurement channel starts from each detector or detector array and the integration intervals of the integrators have been set to be shorter than the overall imaging period; at least one memory unit in the memory means for each measurement channel for storing a plurality of predetermined exposure values; and a calculating unit (23) which compares each integral obtained from the different channels with an exposure value prestored in the memory unit of the corresponding channel and produces a combined effect result of the comparison results, which is fed in the adjustment means (3).

22 Claims, 3 Drawing Sheets

EXPOSURE AUTOMATICS FOR AN X-RAY APPARATUS

BACKGROUND OF THE INVENTION

The invention relates to a method for automatic exposure adjustment of the image receptor in panoramic, tomographic or similar radiography, in which the radiation emitted from a radiation source passes through the object to be X-ray examined, from one area to another, simultaneously displaying the object on an image receptor over an imaging period consisting of such successive stages, the method involving measurement of the intensity of the radiation incidence on the image receptor in the radiation movement direction by means of at least two detectors located behind the receptor, the measurement signals from the detectors and predetermined reference values being used to adjust at least one variable affecting the image receptor exposure during imaging. The invention also relates to an apparatus for implementing this method.

An arrangement for automatic exposure adjustment in panoramic radiography has been disclosed in patent specifications such as FI 69559 and FI 90617. The arrangements described measure the radiation intensity in the area of the film plane, and either the X-ray tube current or the rotation speed of the X-ray unit is adjusted. FI patent specification 69559 does not define the location of the radiation detector, whereas FI 90617 utilises the radiation emitted from a fluorescent plate disposed in connection with the film. These references do not refer to the kind of measurement reference value used for the adjustment. Moreover, we note that a change of the rotation speed, i.e. exposure time of a panoramic X-ray apparatus in operation results in images of extremely poor quality. U.S. Pat. No. 4,021,672 describes an automatic regulator of a similar type, using a detector placed behind the X-ray film, and adjusting other variables affecting exposure by means of a reference value, except for the rotation speed of the panoramic X-ray apparatus. EP patent specification 229 972 further describes a similar automatic regulator, in which the detector or detectors are placed either in front of or behind the film, and are used to adjust the exposure variables by means of a reference value. Apart from this, the reference mentions a choice method, allowing the appropriate speed to be chosen among preselected exposure speeds for varying jaw structures. In all of the references described above, a signal that has passed through the object during panoramic radiography is continuously measured, and on the basis of this measurement, either the rotation speed of the panoramic device, or the X-ray tube current, or optionally the X-ray tube voltage is adjusted. Such an arrangement entails a number of drawbacks. Firstly, continuous measurement and continuous adjustment are extremely sensitive to local deviations for instance in the patient's denture. Thus, if the detector detects a significant drop in the radiation intensity, perhaps caused by a tooth filling, the automatic adjustment counteracts by increasing the radiation considerably, thus generating markedly overexposed line on the X-ray film at this point. In an exactly corresponding way, an underexposed line may be generated for instance due to a missing tooth, or there may be other exposure irregularities caused by an irregular denture or jaw bone. Consequently, for instance regarding the patient's denture, the arrangements depicted above will yield a film that is extremely irregularly exposed.

FI patent specification 90618 describes an arrangement in which one or more detectors fitted behind the image receptor in the radiation movement direction measures the radiation intensity that has passed through the patient at short intervals. The general embodiment of this arrangement does not have substantial benefits over those described above, since this automatic control may yield films that are extremely irregularly exposed in exactly the same way. The troubles may be somewhat reduced if the signals from several detectors are combined during intensification. The specification also mentions a measurement technique carried out by measuring the pithel layer subsequent to the jaw bone, and by using this measurement result to adjust the exposure values to remain unaltered over the entire measurement period. Equivalent techniques have been described in patent specifications FI 76234 and U.S. Pat. No. 5,386,448. Hence, the preferred embodiment in the three of these references is to proceed such that the intensity of the beam that has passed through the object is detected before the actual X-ray examination is started in the edge area of the jaw bone, and on the basis of the measurement value or values obtained after this, the movement speed of the panoramic X-ray apparatus is maintained constant during imaging and the voltage and current of the X-ray tube are maintained constant during imaging. In this manner, this arrangement will not have the drawbacks of the continuous measurement and control processes described above, in other words, individual imperfections in the patient's denture will not entail local exposure errors in the X-ray film. However, this does not have to do with a measurement carried out in course of the X-ray examination, since the measurement has been carried out explicitly before the actual imaging, and this proceeding, in turn, has the drawback of the point measurement not necessarily being very representative of the entire area measured. In fact, the point of the patient's jaw bone measured may have greater or smaller relative thickness than the denture area, or the measurement may have taken place at a point that is not otherwise representative, yielding a final image which is either overexposed or underexposed. In all the arrangements described above, problems are caused by the fact that intensity detection is usually performed at one single point, usually having a very small area, and thus it may be very doubtful whether it is representative.

JP patent specification 60 59700 describes a detector consisting of a large number of detector units placed very close to each other to form a matrix. In this way, the impact of an irrelevant point included in the range of measurement of the detector configuration will of course be reduced, given that the outputs of all the detectors have been interconnected, i.e. connected in parallel, and only the summed signal of the detectors is arranged to adjust the exposure. Inversely, however, one may note that the impact of a perfectly relevant measurement point included in the measurement range of the detectors will be quite equally attenuated compared to the impact of non-relevant points, and in that case the measurement result and hence the adjustment result will not improve at all, or to a very small extent, compared to the arrangements described above, using one single small-sized measurement sensor.

In most of the measurement arrangements of the references described above, the detector or detectors measuring the X-radiation intensity are placed behind the film or the film cassette viewed in the X-ray tube direction. Thus the radiation intensity reaching the detector will be very low, since the X-ray film with its exposure intensifying plates will attenuate the radiation significantly. Thus, a detector placed in this way will receive only approx. 30 to 40% of the radiation incidence on the film. Because of this, the signal of a detector placed like this will contain a considerable amount of noise, the signal to noise ratio being extremely poor and the exposure adjustment accuracy also being poor. If the sensor is placed in front of the film cassette, one has either to use very expensive detectors, such as ionisation chambers, to avoid their appearance on the image, or then detection has to be performed before the actual imaging is started and the detectors must be removed for the time of the imaging, resulting in the drawbacks described above. FI patent specification 90617 does mention a light intensifying plate fitted in front of a detector placed behind the film cassette, however, this does not improve the situation very much, because the radiation incidence will in any case have dropped to one half—one fourth of the radiation incidence on the X-ray film. The detectors connected in parallel as described in patent specifications JP 60 59700 and U.S. Pat. No. 4,021,672 improve the signal to noise ratio only to a small extent, because the noise voltage increases in such arrangements almost at the same rate as the effective-signal level. None of the references cited above describes an arrangement for automatic exposure adjustment in tomography.

SUMMARY OF THE INVENTION

A first object of the invention is to achieve a method and a device for automatic adjustment of the exposure in an image receptor during imaging, which is suited for use both in panoramic radiography and tomography. A second object of the invention is a method and an arrangement for automatic adjustment of the exposure in the applications described above, in which the detectors can be placed behind the image receptor seen in the radiation movement direction, still yielding a high-quality signal with a good signal to noise ratio. A third object of the invention is a method and a device of the type described above, in which the intensity having passed through the object can be detected during panoramic and tomographic X-ray examination and the exposure can be adjusted during the proceeding such that any individual points in the object in focus causing intensity errors do not at least significantly affect the correct setting of the exposure values. A fourth object of the invention is such a method and a device which can be accomplished with simple and economical components.

The drawbacks described above are eliminated and the objects defined above are achieved with the method in accordance with the invention, which is characterised by the features defined in the characterising clause of claim 1, and with the device in accordance with the invention, which is characterised by the features defined in the characterising clause of claim 11.

The chief advantage of the invention is that the use of the method and the device of the invention provide a control signal from detectors placed behind the image receptor, thus not visible on the final image, to the adjustment device, with a very good signal to noise ratio. A second advantage of the invention is that the outcome above is achieved by using simple and relatively economical components in the apparatus, without having to resort to expensive special components. A further advantage of the invention is that the use of its method and device effectively eliminates the impact on the exposure adjustment of exceptional points in the patient, such as tooth fillings, gaps or similar, so that the entire image receptor will be correctly and evenly exposed.

BRIEF DESCRIPTION OF THE DRAWINGS

The invention will be described below in greater detail and with reference to the accompanying drawings.

DETAILED DESCRIPTION OF THE INVENTION

Figure 1:
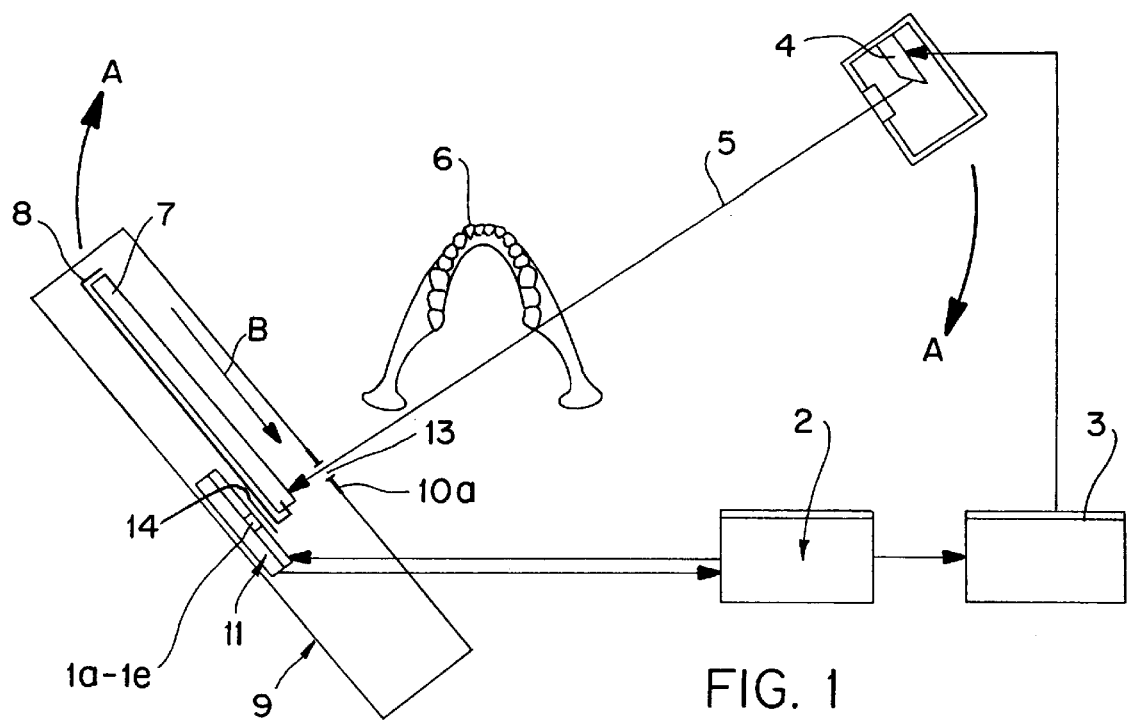
FIG. 1 is a schematic top view of the panoramic X-ray apparatus in accordance with the invention.

FIG. 1 illustrates a panoramic X-ray apparatus consisting of an X-ray source 4, from where the X-ray beam 5 passes via a primary blind not represented in the figure in the form of a narrow cone of rays 5, whose height is perpendicular to the image plane. In the image plane direction, the cone of rays 5 is very narrow, as can be understood from the figure. This cone of rays 5 passes through the object in focus 6, in this instance the jaw bone and the denture, and further to the image receptor 7 in the panoramic X-ray apparatus. In front of this image receptor 7, facing the X-ray tube 4, there is a secondary blind 10a, with a slot 13, whose height H in a direction perpendicular to the plane of FIG. 1 equals the height of the image produced and whose width W1 in the direction of the plane in FIG. 1 and thus of the image receptor 7 is small compared to the length of the image receptor, being in the general range of 1 to 3 mm or close to these prior art values. The image receptor 7 is fixed to a stand 8 and this assembly is placed in a receptor casing 9. The secondary blind 10a is stationary in the casing 9, but the image receptor stand 8 moves the image receptor 7 in the direction of arrow B during imaging, while the X-ray tube 4 and the receptor casing 9 rotate about an axis perpendicular to the image plane, not represented in the figure, in rotation direction A. In this way, as the X-ray tube and the receptor casing rotate in direction A and the image receptor 7 moves in a direction B opposite to rotation A under the rotation of its stand 8, the image receptor 7 will be exposed over its entire surface via the slot 13 in the secondary blind 10a in a manner known per se. In addition to this, the panoramic X-ray apparatus naturally includes an X-ray generator 3 and a control unit 2 for this, used to control the X-ray tube current and acceleration voltage.

Figure 3:
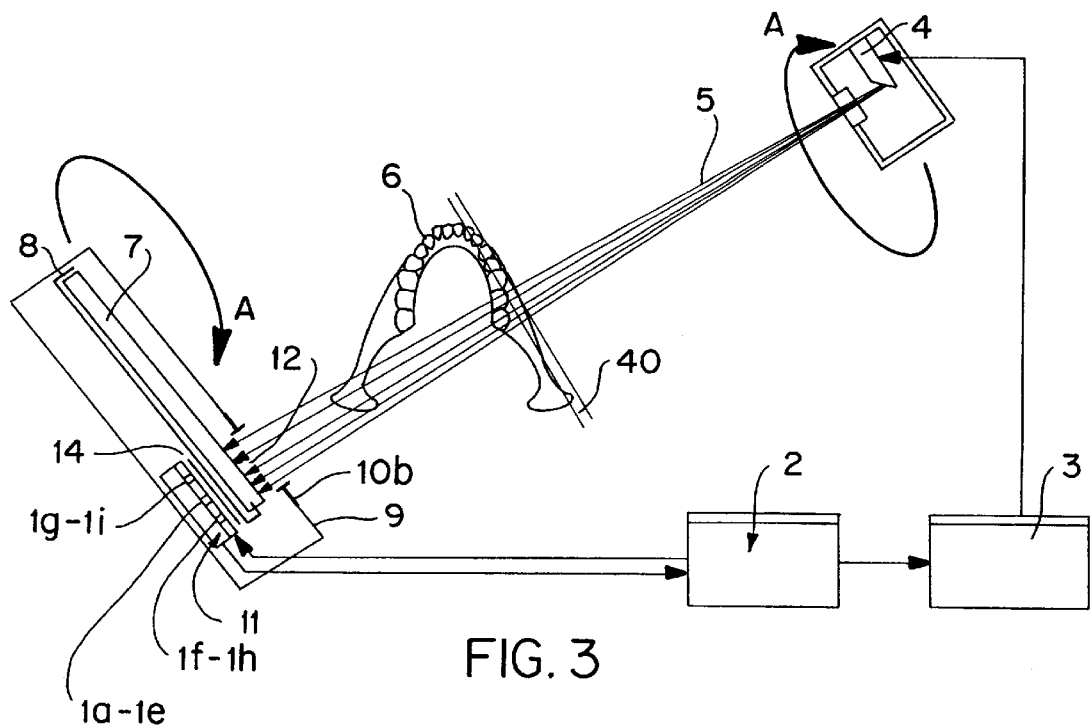
FIG. 3 is a schematic top view of the tomographic device in accordance with the invention.
Figure 4:
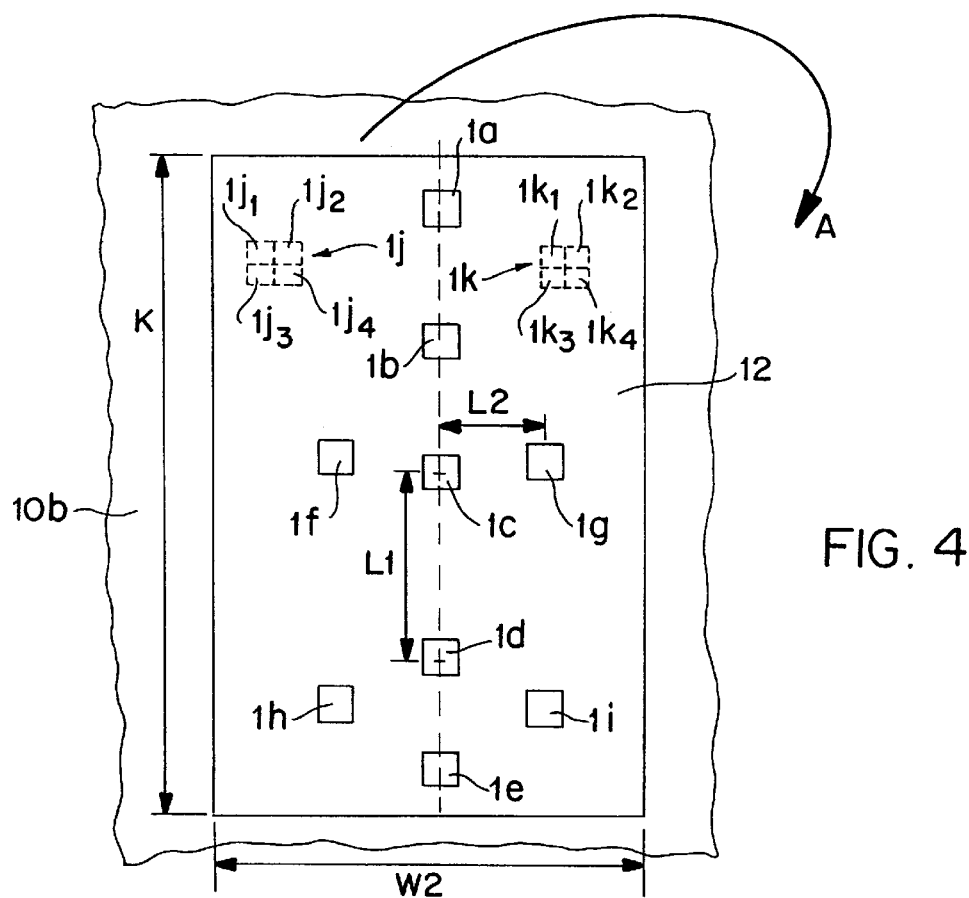
FIG. 4 shows the image field of the device in FIG. 3 and detectors placed behind the image receptor viewed in the travel direction of the X-ray beam.

FIG. 3 illustrates a tomographic apparatus, which includes an X-ray tube 4, which emits, via an opening in a primary blind not represented, a cone of rays 5, whose cross-area at the image receptor 7 equals the surface of the image desired. In this way, the cone of rays 5 will have the vital dimensions both in a plane parallel with FIG. 3 and in a direction perpendicular to this, as can be understood from FIG. 3. This cone of rays 5 then passes anew through the object in focus 6, in this instance the jaw bone and the denture, with incidence over the entire image field 12 of the image receptor 7. The image field has a height H and a width W2, as can be seen in FIG. 4, and this image field 12 is usually limited with a secondary blind 10b in order to prevent scattered radiation from reaching undesired areas. In this case, the image receptor 7 and the stand 8 supporting it are fixed in position relative to the receptor casing 9. With a subsequent move of the X-ray tube 4 and the receptor casing 9 in planes perpendicular to the cone of rays or on spheric surfaces perpendicular to the cone of rays such that the cone of rays 5 remains constantly directed to the image field of the image receptor 7, a virtual or an apparent lens will be produced, i.e. no physical real lens, which displays a given plane or layer 40 of the object 6, which is perpendicular to the cone of rays 5, with full or adequate sharpness on image receptor 7. In the most straightforward case, the X-ray tube 4 and the casing 9 are moved in one single plane, producing an image called linear tomograph, however, in most cases the X-ray tube and the receptor casing are moved in planes perpendicular to the cone of rays or on a spheric surface perpendicular to the cone of rays in different directions, e.g. along a circular line, spirally or following a hypocycloid, or along any other suitable curve, at the same time as the movement of the receptor casing is inversely symmetrical to the movement of the X-ray tube relative to any point in the cone of rays 5 between these. Depending on the type and extent of the movements of the receptor casing and the X-ray tube, the thickness of the layer 40 of the object 6 will be regulated, which in each case is sharply displayed on the image receptor 7. The object areas over this plane will not be sharply X-ray photographed on the image receptor in terms of optical rules, but instead, they will produce only minor signal attenutation, although the cone of rays 5 passes through the areas of these objects in focus. In this case as well, the apparatus further comprises an X-ray generator 3 and a control unit 2 controlling its current and voltage. In FIG. 3, the curved arrows A indicate the inversely symmetrical movements, known per se, of the X-ray tube 4 and the receptor casing 9 described above.

Besides the arrangements depicted above, the image receptor 7 may naturally consist of fluorescent plates, called light intensifying plates, placed on one or either side of it, in addition to the film and of any other ordinary components not shown in the figure. Hence these components will not be explained in further detail in this patent application.

In accordance with the invention, at least two detectors 1, interspaced by distance L in the vertical direction H of the slot, are placed behind the image receptor 7 of the panoramic X-ray apparatus, viewed in the incidence direction of the cone of rays 5, at the cone of rays, i.e. at the slot 13 of the secondary blind 10a. Thus, this distance L is perpendicular both to the movement direction B of the image receptor 7 and to the movement direction A of the receptor casing 9, these movement directions thus being inverse. Similarly, at least two detectors 1 are disposed behind the image receptor 7 in the tomographic apparatus, viewed in the incidence direction of the cone of rays 5, in the image field 12, i.e. the stationary image field 12 defined by the secondary blind 10b, the detectors being interspaced by a vertical distance L1 or a distance L2 perpendicularly horizontal to this. In this patent application, the general reference 1 is used for detectors both in terms of panoramic radiography and tomography, and to emphasise a detector property, the specific references 1a, 1b, 1c, etc. are used.

Figure 2:
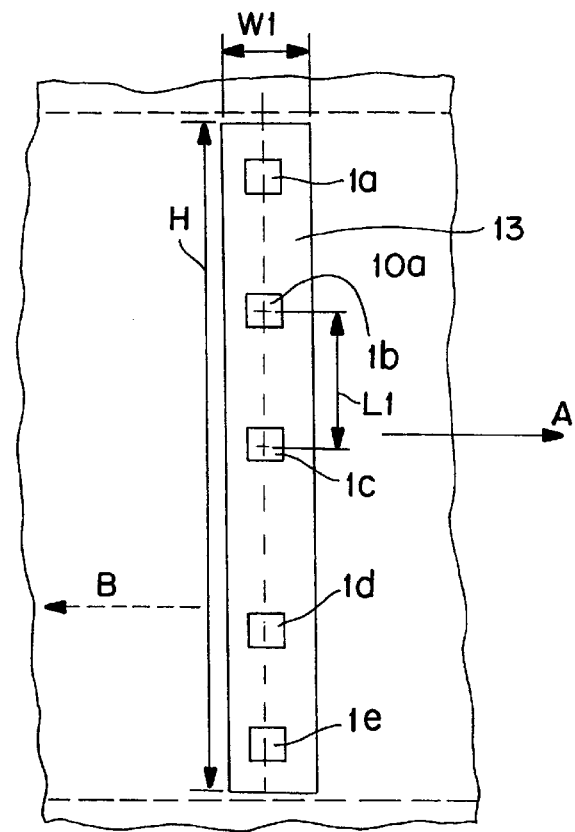
FIG. 2 shows the secondary blind opening in front of the image receptor in the apparatus and detectors placed behind the image receptor viewed in the travel direction of the X-ray beam.

The panoramic X-ray apparatus typically includes at least three, preferably four or five detectors in the vertical direction H of the image field, such as detectors 1a–1e in FIG. 2. The vertical distances L1 between these detectors may be mutually equal or different, however, such detectors are typically provided over the total height H of the image field. In this conjunction, however, it should be noted that the image field length in panoramic radiography will be at least nearly equal the length of the image receptor 7 in its movement direction B, which is multiple compared to the width W1 of the secondary blind slot 13. In this case, detectors 1a–1e are typically placed in an array parallel to the slot 13 of the secondary blind 10a, as indicated with broken lines in FIG. 2, owing to the narrow slot 13. However, there is nothing to prevent the detectors from being disposed in the slot 13 of the secondary blind in any other way.

In a tomographic apparatus, a plurality of detectors 1 are typically interspaced by both vertical distances L1 and horizontal distances L2, and preferably at points remote from each other, implying that they will be provided at several points on the image field 12, and not in any case concentrated at one point of the image field. The detectors 1 may be distributed over the image field for instance interspaced by equal vertical distances L1 and equal horizontal distances L2, in other words, regularly distributed over the image field. In a tomographic device, at least four interspaced detectors are typically used, placed in mutually perpendicular directions L1 and L2, e.g. detectors 1f–1i, and preferably there are e.g. five detectors, such as detectors 1a, 1e, or nine detectors, as indicated in FIG. 4 with detectors 1a–1i. Detectors 1 may be horizontally disposed at at least three points on the image field 12, thus interspaced by two horizontal distances L2, as in FIG. 4, and also vertically at at least three points, thus interspaced by two vertical distances L1. In the event that there are only four detectors, they may be disposed for instance at the corners of an imagined rectangle within the image field 12, and if there are five or more detectors, some of these detectors can be placed inside or outside this rectangle, as shown in FIG. 4. In any case, the detectors will be interspaced by both vertical and horizontal distances, so that, under the joint effect of these distances, detectors 1 will always be interspaced by distances perpendicular to the movement direction A of the image receptor, or accordingly, by distances perpendicular to the movement direction of the cone of rays, irrespective of the type of movement A adopted in tomography, for instance any of those described above. Thus, in tomography, the movement direction A will differ with continuous variation both from the height K and the width W2 of the image field 12, the height being nevertheless vertical and the width horizontal.

Whenever necessary, both a panoramic and a tomographic X-ray device may comprise, in addition or instead of separate detectors 1a–1e and 1a–1i, an array of several detectors, such as a detector matrix 1j and 1k, marked with a dotted line in FIG. 4. In this case, both the detector matrices consist of four part detectors $1j_1$–$1j_4$ $1k_1$–$1k_4$ placed in a square. The outputs of the individual detectors in such a detector matrix are frequently, but not necessarily, connected in parallel as explained below.

The detectors 1a–1e and 1a–1i, respectively, used in the device covered by the invention, are any diodes, transistors, or similar means sensitive to the X-radiation used. In this instance, these sensitive diodes or transistors and the image receptor are preferably interspaced, on the side of the diodes or transistors facing the radiation source 4, by a fluorescent plate 14, which may be a common plate for all of or some of the detectors, or separate for each detector. In the most straightforward embodiment, this fluorescent plate 14 is made of the same material as the material used as light intensifying plates with X-ray films. By these means, the signal obtained from the detectors will be intensified, given that detectors are normally sensitive also to the radiation emitted by a fluorescent plate. Of course, there is nothing to prevent also other types of detectors from being used, such as photomultiplying tubes or the like, however, such detectors are expensive.

As the receptor casing 9 in a panoramic X-ray apparatus is moving during the motion of the image receptor around the object 6 in focus under the effect of the rotational movement A, and the cone of rays 5 following this movement, the detectors 1a–1e will receive continuously variable radiation that has passed through the object during imaging. Accordingly, in tomography, as the receptor casing 9 is moving on a plane or spherical surface perpendicular to the cone of rays 5 along a predetermined path A relative to the object 6 in focus, and the cone of rays following this movement, the image field 12 will receive continuously variable radiation through the object 6 in focus, thus generating continuously variable radiation intensity in the detectors 1a–1i. In accordance with the invention, the continuously variable measurement signals generated by the continuously variable radiation intensity reaching these detectors 1a–1e and 1a–1i respectively are immediately and separately integrated, independently of the measurement signals from the other detectors. In principle, this means that the measurement signal obtained from the output of each detector 1a–1e and 1a–1i respectively is immediately integrated without using any intermediate amplification, and integration is usually performed over a specific predetermined time interval. In accordance with the invention, the output signal of each detector 1a–1e and 1a–1i is preferably consistently integrated, whereas the integration outcome is read at intervals corresponding to the integration period mentioned above. Nevertheless, nothing prevents the subsequent integration from being initiated at the end of each integration interval. The result obtained in these two cases is completely identical, only the coupling details being different, as an electronics expert will well understand, and thus these particular couplings will not be explained in this patent application. The duration of each individual integration in accordance with the invention is substantially shorter than the overall imaging period in panoramic radiography or tomography. In accordance with the invention, the value of each individual integration, i.e. the integration outcome value that has been read, is compared with the target value for the corresponding predetermined exposure, and the difference signal obtained from this is used to adjust at least on of the variables affecting the exposure of the image receptor so as to, for this purpose, take account of the combined effects of the integration results read from all of the detectors. The exposure target value is the integrated value obtained from the radiation that has passed through a typical object over a time interval corresponding to the integration interval to be implemented during imaging and which has been confirmed to yield the correct exposure for the image receptor used. The exposure target value once measured can of course be adapted to each type of receptor, say, if receptors with varying sensitivity are being used.

Figure 5:
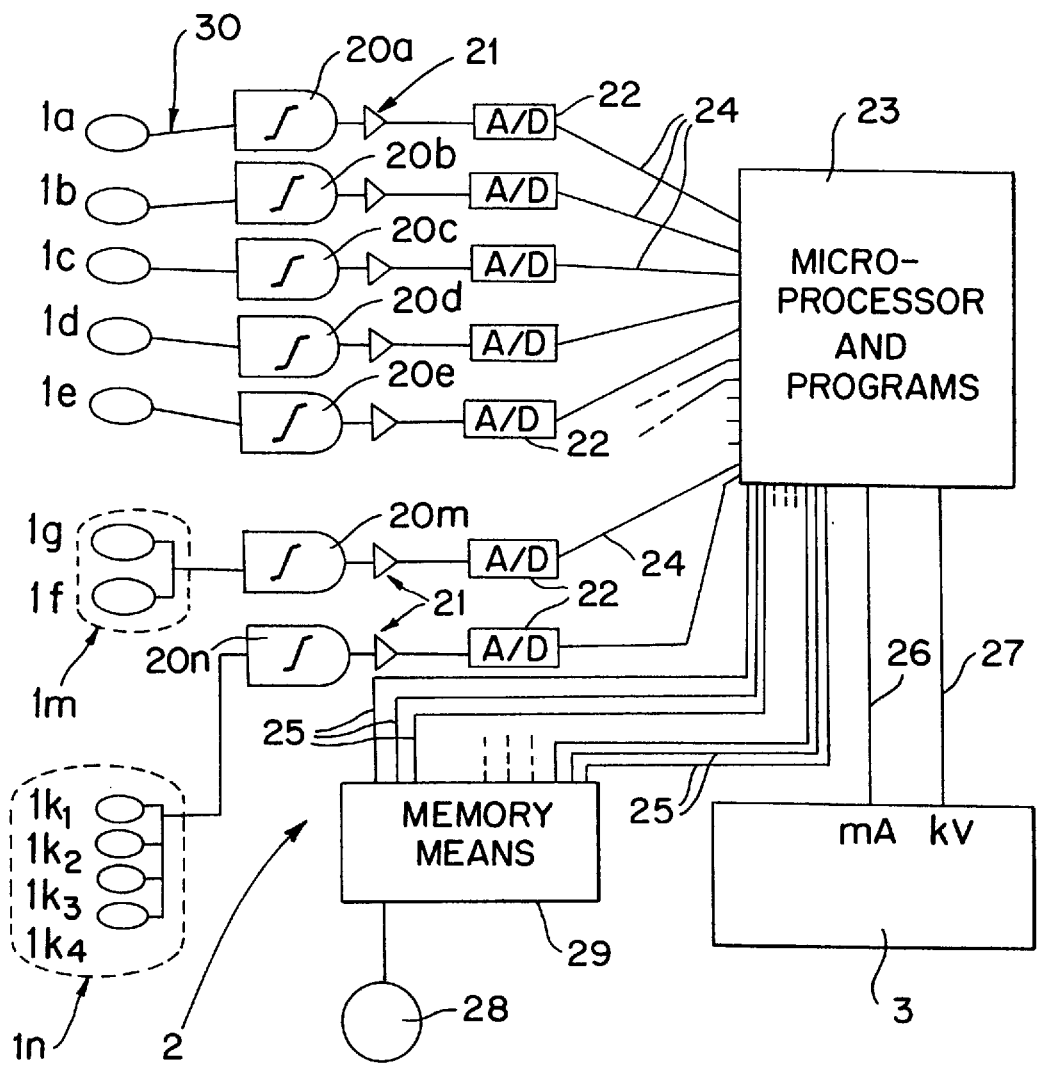
FIG. 5 shows the block diagram principle of a coupling arrangement that can be used in the method and the device in accordance with the invention.

FIG. 5 is a block scheme of the coupling producing the operation of the invention as described above. The figure shows the individual detectors 1a–1e, whose outputs 30 are directly connected with the inputs of the integrators 20a–20e, i.e. each detector has an integrator of its own, which integrates the signal emitted from the detector directly, without intermediate amplification. When desired, the outputs of the detectors disposed at various points on the image field 12 or the secondary blind slot 13 can be interconnected and this coupling point can be directly connected with the input of their common integrator. Thus, as shown in FIG. 5, the outputs of e.g. detectors 1g and 1f in FIG. 4 are interconnected and connected directly to the input of integrator 20m, these detectors thus forming a detector array 1m. Likewise, the outputs of detectors $1k_1$–$1k_4$ in detector matrix 1k are directly interconnected and directly connected with the input of integrator 20n, the detectors thus forming the detector array 1n. In these cases as well, the integration is carried out directly from the detector outputs without intermediate amplification. The parallel connections of the detector outputs described above are of course but exemplifying, and in practical operation, detector outputs are connected in parallel only in cases where it is considered necessary for the outcome. In short, the principle of the invention is that the output signal obtained from one or more detectors is immediately integrated without any actual intermediate amplification. As a result of this direct integration, especially the signal to noise ratio is substantially improved compared to prior art. In fact, if the signal obtained from the detector were initially amplified, this would deteriorate the signal to noise ratio compared to the ratio in the detector output because of the additional effect of the amplifier's own noise and the offset voltage. An increase in the sensitive area of the detectors, i.e. parallel connection of the detectors, does improve the signal to noise ratio to some extent, yet the arrangement of the invention improves it significantly more. As described above, beside the integration arrangement of the invention, parallel connection of the detectors can also be utilised, provided that no preamplifier is being used at an intermediate stage. Under the action of the fluorescent plates used in front of the detectors, the signal to noise ratio also improves, but in fact, this proceeding can also be adopted in addition to the integration procedure of the invention, and in that case the signal to noise ratio is even further improved. Thus, the most vital feature of the invention is that the signal obtained from the detectors is integrated over a specified time interval as close to the detector outputs as possible, and this is done by avoiding any intermediate amplifiers as much as possible. Such an integration procedure significantly improves the signal to noise ratio compared with prior art solutions and yields appreciably more accurate adjustment results.

As described above, from each detector 1a–1e etc. starts an individual measurement channel 24 and accordingly from each detector array 1m and in starts a corrsponding measurement channel 24. Thus, each of these measurement channels has integrators 20a–20e, 20m and 20n, etc. of their own. When necessary, these integrators, generally marked with reference 20, are followed by an adapting amplifier 21, which adapts the quality of the integrated signal to the input of the subsequent A/D converter 22 on each channel 24. Typically, the signal is subjected to current-voltage conversion in the adapting amplifiers. From the output of these A/D converters 22, the measurement channels 24 are further taken to a microprocessor 23. The equipment also comprises memory means 29, including a plurality of first memory units, at least one for each measurement channel 24. In each first memory unit, several predetermined exposure values have been stored, each corresponding, in accordance with the invention, to the expected values for successive integration intervals or integration result readings. The microprocessor 23 thus compares the value of the integration result read on each channel 24 after each individual integration interval with a corresponding predetermined expected radiation value stored in the corresponding first memory unit of the corresponding memory means 29, and after this the microprocessor carries out a comparison and obtains the difference signal as a result. Hence the number of such difference signals equals the number of measurement channels 24 and of first memory units and signal channels 25 from these. At the end of each integration interval, a plurality of difference signals is obtained, which includes a number of difference signals equal to the number of channels. After this, the microprocessor calculates the combined effect result from this plurality of difference signals in the manner described below, and the result is fed in the X-ray tube generator 3 with a view to adjust the variables affecting the image receptor.

In addition to this, the memory means 29 include second memory units for storing the preset initial exposure values with which the actual panoramic, tomographic or similar radiography is started. There are several such preset initial exposure values, i.e. milliampere values (mA), kilovolt values (kV) for the X-ray tube, and perhaps motion speeds A of the apparatus, and they may be grouped according to patient groups, such as sex, age and various combinations of these, or in any other manner. These initial exposure values may also be selected on the basis of a preliminary measurement conducted before the actual imaging. The number of such second memory units required is only such that the three variables affecting exposure above are stored for the desired number of different patients. The choice of initial exposure values can be made e.g. by means of a regulator 28 or on the basis of previously stored patient data, which the device uses to select the initial exposure values assumingly appropriate for X-raying the object.

In accordance with the invention, the integration durations of integrators 20a–20n are so short over the entire imaging process that the measurement signal of each detector or detector array is integrated at least five times. In a preferred embodiment of the invention, the integration duration is constant and identical for all of the integrators in the apparatus. The integration interval is preferably made so short that at least ten integrations and typically 30 to 100 integrations take place over the entire panoramic or tomographic X-ray examination, and in this case, as described above, each integration implies the integrated value, and if necessary, resetting the integrator. Thus, the integration duration will be in the range of 20 ms to 1000 ms and preferably in the range of 70 ms to 300 ms. In the memory means 29 of the device, in the first memory units, a target exposure value corresponding to the end of each integration interval and each detector or detector array has been stored in order to obtain difference signals. Consequently, if for instance in the panoramic X-ray examination of FIG. 2, the five integrations above are carried out with the five detectors 1a–1e of FIG. 2, a total number of 25 readings have been stored in the memory means 29. To these five first readings correspond e.g. readings expected at detectors 1a–1e in the area of the object 6 in focus, i.e. the area of the jaw bone edge. The subsequent five readings correspond to the corresponding expected readings for the positions of the five detectors 1a–1e in the central area of the left half of the jaw bone, the third five readings correspond to the expected readings at detectors 1a–1e in the area of the jaw bone tip, and the fourth and fifth expected readings correspond to the values of the positions of the detectors 1a–1e in the central area of the right half of the jaw bone and the remaining edge. The example above is but a simplified example, serving to facilitate the understanding of the comparison below and not necessarily corresponding in any way to the considerably more complex comparison criteria used in a real-life apparatus. In accordance with the invention, at the end of each integration interval, the value obtained by integration from each detector is compared with the expected value at the point concerned, which has been stored, as described above, as a reading in the first memory unit of the memory means. In this case, the integrated measurement result provided by five overlapping detectors is compared with a corresponding exposure value stored in the first memory unit which is expected at this point of the jaw bone and which provides the correct exposure for the image receptor. By means of the five difference signals thus obtained the microprocessor 23 adjusts the values mA and/or kV fed by the X-ray generator 3 into the X-ray tube 4. The microprocessor 23 primarily adjusts the X-ray current (mA) along bus 27, but it may also adjust the X-ray tube voltage (kV) along bus 27. The microprocessor keeps these adjusted X-ray tube values constant until the following time the integrated measurement values are read. If, in the case of FIG. 1, the five detectors mentioned above are being used, but integration takes place ten times, 50 expected exposure values will have been stored in the first memory units of the memory means 29, and if integration takes place 100 times, 500 expected exposures values will have been accordingly stored in the memory units. Similarly, in tomography, if the nine detectors in FIG. 4 are each used separately, and ten integration operations are carried out during the procedure, 90 expected exposure values will have been stored in the memory means, and if there are 100 integration operations, 900 expected exposure values have been stored in the memory unit of the memory means. The number of stored exposure target values evidently depends on the integration duration, besides the number of detectors and thus the number of measurement channels. The numeric value of the expected exposure values stored in the first memory units of the memory means 29 correspond to the value obtained by similar integration at a typical object, and not to a momentary signal value, for the measured values and the stored values to remain mutually comparable.

Consequently, the method and the device in accordance with invention operate as follows. Before the imaging process is started, the apparatus determines the exposure values probably suitable for the patient's object to be X-ray examined on the basis of patient type data provided or stored or any appropriate preliminary measurement, and thus the motion speeds for the X-ray tube 4 and the image receptor casing 9, the X-ray tube voltage kV and the X-ray tube current mA. During the imaging process, the exposure automatics in accordance with the invention does not at least primarily alter the apparatus motion speeds A and B to yield a good image result. After this, the actual panoramic radiography or tomography is started, during which detectors 1a–1e or 1a–1i or any other similar detectors located behind the image receptor 7 receive a specific radiation, which depends on the penetration at various point of the object 6. During imaging signals received from the detectors 1 are integrated as described above. When, for instance, the constant integration interval comes to an end, each measurement value obtained by integration is compared with reference values stored in the first memory units of the memory means, and using the difference signals, the microprocessor calculates, by means of a program explained in detail below, changes in the X-ray tube values, i.e. either in the voltage or the current. Most frequently the X-ray tube current mA alone is regulated. The panoramic or tomographic radiography continues over the entire process at an even rate, and at the end of each integration interval the operation above is carried out, after which the set values for the X-ray tube are maintained until the end of the subsequent integration interval. In this manner, the entire image receptor 7 will be exposed without sudden changes in the exposure value, however, still taking account of the penetration of the object 6. The proceeding above yields an excellent adjustment result also because there will be minimum impact of interference signals such as noise. Radiography of some other kind than that described above, radiation detection may be conducted also with regard to a moving cone of rays.

Besides the target exposure values stored in the first memory units of the memory means 29, a predetermined exposure maximum and/or minimum value may preferably be stored in the memory means, these values being used as follows. If the integrated measurement signal obtained from detector 1 exceeds the predetermined maximum value or is under the predetermined minimum value, it may be concluded that there is an exceptional area in the object 6 in focus, such as a tooth filling or any cavity. For this eventuality, the microprocessor 23 has been programmed such that the difference signal between the exposure target value and the measured value will not be used at this exceptional point, but instead this exceptional measured signal will be replaced either with one previous integration value for the detector, or with the mean value of several previous integrations, or with the weighed mean value of several previous integrations, or with any predetermined value. This means that a measurement value that differs too much, i.e. more than by a specific deviation value, from the preset exposure target value will be rejected and replaced with another value as described above.

The description above refers to a preferred embodiment of the invention, where the integration durations have been set to be constant. Thus, at the end of each integration interval, the integrated measurement signal obtained is compared with corresponding integrated target values stored in the memory means 29. However, the integration durations may optionally be variable, and then the comparison between the measurement signals and the signals stored in the first memory means can be carried out in two optional ways. First, the moment of comparison between the measurement signals and the exposure values stored in the memory means can be determined as the moment when a predetermined proportion of all the integrated measurement signal values provided by the detectors 1 equals or exceeds the exposure values predetermined for them and stored in the first memory units. After this the measurement signal value obtained from each detector can be compared at this moment with the exposure values stored in the first memory units of the corresponding memory means, after which the microprocessor will adjust the X-ray tube values on the basis of the difference signals. Optionally, the microprocessor may be arranged to define the difference between the time it takes to reach the predetermined value obtained from each detector and stored in the first memory units and the predetermined target integration interval. On the basis of the time differences obtained from each detector, the microprocessor then adjusts the X-ray tube values. Hence the difference between these two ways of proceeding is that in the first one, the intensity of the integrated measurement signals obtained from the detectors at a given moment are compared with the intensity of the values in the memory, whereas in the second one, the difference between the integration intervals and the target integration intervals required for a given signal intensity are mutually compared.

The final outcome of the three different proceedings is the same in practical operation, yet equipment details and the microprocessor programming must of course be adequately adapted to each way of proceeding.

The detectors 1 used in the apparatus in accordance with invention may be of any conventional type suitable for the purpose and similarly, the integrators 20 may be of any usable type available on the market, and also, the buffer amplifiers 21 and the A/D converters 22 may be of any suitable type available on the market. The microprocessor 23 may be an ordinary processor with firm logic, and to calculate the combined effect result, it may use either a fixed, predetermined set of rules or a variable set of rules, i.e. fuzzy programming, corresponding to fuzzy logic. An actual processor without firm logic may also be used, and in that case the combined effect result is calculated with a variable set of rules, i.e. fuzzy logic. In any case, some kind of mean value is calculated from the difference signals described above in order to adjust the X-ray tube values through the buses 26, 27. Depending on the type of program used in the processor, this mean value may be calculated in considerably different ways and even in variable ways when the fuzzy programming or fuzzy logic mentioned above is being used.

I claim:

1. A method for automatic adjustment of image receptor exposure during imaging in panoramic or tomographic radiography, comprising the steps of:

passing radiation emitted from a radiation source through an object from one area to another area;

moving the image receptor and radiation source relative to each other during an imaging period at a preset speed to expose said receptor to the radiation;

displaying the object over the imaging period on the image receptor;

measuring varying intensity of the radiation incidence on the image receptor by means of at least two detectors placed behind the receptor to produce a plurality of measurement signals;

immediately and separately integrating over an integration time interval the measurement signal obtained from each detector during the imaging period to produce an integral for each detector, whereby the integrating of each measurement signal occurs independently of the integrating of other measurement signals, the integrating is implemented over the entire imaging period, and the integration time interval is substantially shorter than the imaging period to produce a plurality of individual integrals for each detector during the imaging period;

comparing each individual integral with a corresponding predetermined exposure value to produce a comparison value; and determining an adjustment value on the basis of said comparison values corresponding to each of the detectors and using said adjustment values to adjust during said imaging period at least one of a plurality of x-ray source variables affecting the image receptor exposure.

2. The method of claim 1, wherein the integration time intervals are such that the measurement signal from each detector is integrated at least five times over the imaging period; the variables affecting the image receptor exposure are adjusted according to the adjustment value at the end of each integration time interval; and each predetermined exposure value is set as a value of intensities corresponding to a target exposure integrated over a specific time interval.

3. The method of claim 1, wherein if the integral deviates from the corresponding predetermined exposure value by a predetermined amount or more, the integral is replaced with a replacement signal, said replacement signal selected from the group consisting of a mean value of preceding integrals of the detector, a weighted mean value of several previous integrals, and a predetermined value.

4. The method of claim 1, wherein the imaging is initiated with a predetermined initial exposure value, said predetermined initial exposure value determined by the object in focus.

5. The method of claim 1, wherein the measurement of the intensity of the radiation incidence on the image receptor is performed substantially over an entire image field:

by disposing a plurality of detectors at interspaced fixed points over substantially an entire image field;

by disposing the detectors to move along with the radiation emitted from the radiation source over the entire image field; or by disposing the detectors to remain at a fixed point within the radiation emitted such that, as the image receptor moves across the emitted radiation, detection will take place substantially over the entire image field.

6. The method of claim 1, wherein the radiation source and the image receptor are each moved at a substantially constant speed over each said imaging period causing a predetermined exposure time for said receptor, and said at least two detectors are arranged to have a spacing perpendicular to a moving direction of the image receptor.

7. The method of claim 1, wherein the integration time intervals are set to be constant and the measurement signals obtained from the detectors are compared with predetermined exposure values at the end of each constant interval.

8. The method of claim 7, wherein the integral from each detector is compared at the end of the constant interval with a corresponding predetermined integrated target exposure value to produce a plurality of difference signals, and at least an X-ray tube current is adjusted on the basis of a mean value of the difference signals between said integrals and predetermined integrated exposure values, said mean value calculated in a predetermined manner.

9. The method of claim 8, wherein the constant integration interval is set to be identical for each detector, said interval remaining identical during the imaging process and in the range of 20 ms to 1000 ms.

10. The method of claim 1, wherein the integration time intervals are set to be variable such that the duration will consist of an interval over which a predetermined proportion of all the measurement signals provided by the detectors equals or exceeds the exposure values predetermined for them.

11. The method of claim 10, wherein the integration interval of each detector is compared at the end of the variable interval with a predetermined target integration interval to produce a plurality of time difference signals, and at least an X-ray tube current is adjusted on the basis of a mean value of the time difference signals, said mean value calculated in a predetermined manner.

12. The method of claim 10, wherein the integral from each detector is compared at the end of the variable interval with a corresponding predetermined integrated exposure value to produce a plurality of difference signals, and at least an X-ray tube current is adjusted on the basis of a mean value of the difference signals between said integrals and predetermined integrated exposure values, said mean value calculated in a predetermined manner.

13. An apparatus for automatic adjustment of image receptor exposure during imaging in panoramic or tomographic radiography, where X-ray exposure of said receptor is carried out area by area of an object (6) over an imaging period, and provided with an emitting radiation source (4) and an image receptor (7), radiation passing through said object placed between the radiation source and the image receptor, said radiation source and image receptor moving relative to each other, said apparatus comprising:

at least two interspaced detectors (1) located behind the image receptor and detecting varying intensities of radiation incidence on the image receptor, and producing outputs corresponding to the detected intensity;

measurement channels (24) starting from each detector or detector array;

memory means (29) having a plurality of first memory units at least one for each measurement channel for storing reference exposure values of the image receptor exposure and adjustment means (3) for adjusting at least one x-ray source variable affecting the image receptor exposure during imaging based on the outputs from the detectors and reference values;

an integrator (20a, 20b, 20c, . . . , 20m, 20n) for each separate detector (1a, 1b, 1c, . . . ) or a detector array (1m, 1n) for integrating the detector outputs over an integration time interval to produce an integral, said integrators connected directly to the detector outputs and each integration time interval being shorter than said imaging period; and a calculating unit (23), said calculating unit comparing each integral obtained from the different channels with an exposure value prestored in the memory unit of the corresponding channel to produce a plurality of comparison results and generating a combined effect result on the basis of the comparison results for said channels, said combined effect result being fed (26, 27) in said adjustment means (3).

14. The apparatus of claim 13, wherein the adjustment means (3) include means for adjusting an X-ray tube (4) current during imaging based on said combined effect result; and the integrators (20) have a set integration interval value in the range of 20 ms to 1000 ms.

15. The apparatus of claim 13, wherein the apparatus is used for panoramic radiography and the detectors (1) are located so as to be interspaced by distances (L1) perpendicular to a movement direction (B, A) of the image receptor (7) and a movement direction of the emitted radiation (5) and parallel with the height (H) of the image field.

16. The apparatus of claim 13, wherein the apparatus is used for tomographic radiography and the detectors (1) are located so as to be interspaced by distances (L1, L2) in any two mutually perpendicular directions.

17. The apparatus of claim 13, wherein expected integrated exposure values expected at the end of all the integration intervals in the measurement channel (24) are stored in each memory unit prior to the imaging period, said expected integrated exposure values corresponding to a specific displayed area of the object (6) in focus.

18. The apparatus of claim 13, wherein the detectors (1) are diodes or transistors sensitive to radiation; and a fluorescent intensifying plate (14) has been disposed in between the detectors and the radiation source (4), said plate amplifying the radiation reaching the detector.

19. The apparatus of claim 13, wherein the memory means (29) includes second memory units for storing a plurality of preset initial exposure values, said preset initial exposure values used to adjust at least one of the variables affecting image receptor exposure at the start of the imaging period; and the apparatus includes means (28) for selecting a particular preset initial exposure value.

20. The apparatus of claim 13, wherein the calculating unit (23) is a processor with firm logic, whereby the combined effect result is calculated with a predetermined set of rules.

21. The apparatus of claim 13, wherein the calculating unit (23) is a processor with firm logic, whereby the combined effect result is calculated with a variable set of rules.

22. The apparatus of claim 13, wherein the calculating unit (23) is a processor with fuzzy logic, whereby the combined effect result is calculated with a variable set of rules.

* * * * *